United States Patent [19]

Ehle et al.

[11] Patent Number: 5,795,482

[45] Date of Patent: Aug. 18, 1998

[54] USE OF HYDROCARBON-SOLUBLE AMINOMETHYLENE PHOSPHONIC ACID DERIVATIVES IN THE SOLVENT EXTRACTION OF IRON IONS FROM AQUEOUS SOLUTIONS

[75] Inventors: Michael Ehle; Knut Oppenländer, both of Ludwigshafen, Germany

[73] Assignee: BASF Aktiengesellschaft, Ludwigshafen, Germany

[21] Appl. No.: 750,984

[22] PCT Filed: Jun. 16, 1995

[86] PCT No.: PCT/EP95/02327

§ 371 Date: Jan. 8, 1996

§ 102(e) Date: Jan. 8, 1996

[87] PCT Pub. No.: WO96/00309

PCT Pub. Date: Jan. 4, 1996

[30] Foreign Application Priority Data

Jun. 23, 1994 [DE] Germany ............ 44 21 932.6

[51] Int. Cl.⁶ ............... C22B 3/38; C22B 3/40; C22B 3/42; C22B 3/26

[52] U.S. Cl. ............ 210/634; 252/364; 423/139; 210/911; 210/638

[58] Field of Search ............ 252/364; 423/139, 423/150.3; 210/634, 638, 639, 911–914

[56] References Cited

U.S. PATENT DOCUMENTS

| | | | |
|---|---|---|---|
| 4,528,167 | 7/1985 | Preston | 210/638 |
| 4,582,691 | 4/1986 | Fujmoto et al. | 210/638 |
| 4,741,831 | 5/1988 | Grinstead | 210/638 |
| 4,758,414 | 7/1988 | Gifford et al. | 423/122 |
| 4,834,951 | 5/1989 | Schwab et al. | 210/634 |
| 5,366,715 | 11/1994 | Dreisinger et al. | 210/912 |

FOREIGN PATENT DOCUMENTS

| | | |
|---|---|---|
| A-0350172 | 1/1990 | European Pat. Off. |
| 1342412 | 2/1964 | France |
| 3801430 | 8/1989 | Germany |
| 970011 | 6/1964 | United Kingdom |
| WO-A-9005115 | 5/1990 | WIPO |
| WO-A-9102011 | 2/1991 | WIPO |

*Primary Examiner*—Thomas G. Wyse
*Attorney, Agent, or Firm*—Oblon, Spivak, McClelland, Maier & Neustadt, P.C.

[57] ABSTRACT

Hydrocarbon-soluble aminomethylenephosphonic acid derivatives comprising the structural element of the formula I

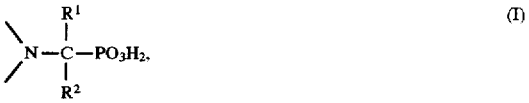

where $R^1$ and $R^2$ are hydrogen, $C_1$–$C_{30}$-alkyl which can additionally bear up to 15 hydroxyl groups and/or be interrupted by up to 14 non-adjacent oxygen atoms, $C_2$–$C_{30}$-alkenyl, $C_7$–$C_{18}$-aralkyl or $C_6$–$C_{14}$-aryl which may be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, for the solvent extraction of iron ions from aqueous solutions.

8 Claims, No Drawings

USE OF HYDROCARBON-SOLUBLE AMINOMETHYLENE PHOSPHONIC ACID DERIVATIVES IN THE SOLVENT EXTRACTION OF IRON IONS FROM AQUEOUS SOLUTIONS

BACKGROUND OF THE INVENTION

FIELD OF THE INVENTION

The present invention relates to the use of hydrocarbon-soluble aminomethylenephosphonic acid derivatives comprising the structural element of the formula I

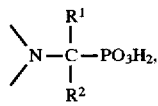
(I)

where $R^1$ and $R^2$ are hydrogen, $C_1$–$C_{30}$-alkyl which can additionally bear up to 15 hydroxyl groups and/or be interrupted by up to 14 non-adjacent oxygen atoms, $C_2$–$C_{30}$-alkenyl, $C_7$–$C_{18}$-aralkyl or $C_6$–$C_{14}$-aryl which can be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, for the solvent extraction of iron ions from aqueous solutions.

The invention also relates to the additional use of certain modifiers for such solvent extractions of iron ions or, generally, metal ions from aqueous solutions.

DISCUSSION OF THE BACKGROUND

The removal of iron ions from aqueous solutions is particularly important in hydrometallurgical nonferrous metal production, eg. in the winning of copper or zinc. Solutions of desired metals are frequently obtained from ores by digestion or leaching with aqueous, usually acid systems. The interfering metal iron has to be removed from these solutions. In addition, the work-up of metal-containing wastes or residues (eg. flue dusts or precipitation sludges from wastewater treatment) and the recycling of used metal products (eg. catalysts) nowadays play an ever more important role in the provision of aqueous solutions of desired metals. Regardless of the origin of the metal salt solutions, it is always necessary to remove interfering elements, in particular the interfering metal iron, from these solutions of desired metals so that pure metals can be isolated. Apart from improving the quality of the desired metals, recovery of the iron and reducing contamination of landfill areas is also sought for economic and ecological reasons.

The solvent extraction of iron ions is known in the literature. Thus, DE-A 38 01 430 (1) describes the use of a mixture comprising a primary amine and an alkylphosphonic monoester such as mono-2-ethylhexyl 2-ethylhexylphosphonate for the removal of iron(III) ions from acid zinc salt solutions by solvent extraction.

Furthermore, JP-A 1985/077936 (2) discloses that aminomethylenephosphonic acid derivatives are suitable for the solvent extraction of uranium, antimony or bismuth.

US-A 4 741 831 (3) relates to a process for separating metals such as iron, cobalt, copper, vanadium, cadmium, nickel, zinc, lead or aluminum from aqueous solutions using water-soluble polymeric complexing agents, for example polyethyleneiminephosphonates. The metal complex is subsequently separated off by dialysis or ultrafiltration by means of membranes.

However, the above processes of the prior art still have disadvantages. They are mostly not efficient enough and are too uneconomical. In particular, the selectivity of the separation of the interfering metals from the desired metals and the loading capacity of the complexing agents used are still in need of improvement.

SUMMARY OF THE INVENTION

It is an object of the present invention to find an improved system for the solvent extraction of iron ions from aqueous solutions which no longer has the disadvantages of the prior art.

We have found that this object is achieved by the use as defined in the introduction of the hydrocarbon-soluble aminomethylenephosphonic acid derivatives having the structural element I.

DETAILED DESCRIPTION OF THE PREFERRED EMBODIMENTS

Preferably, use is made of hydrocarbon-soluble aminomethylenephosphonic acid derivatives comprising the structural element of the formula Ia

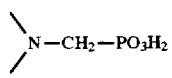
(Ia)

For the purpose described, particular preference is given to hydrocarbon-soluble aminomethylenephosphonic acid derivatives of the general formula II

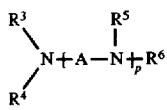
(II)

where $R^3$ to $R^6$ are each hydrogen, $C_1$–$C_{30}$-alkyl which can additionally bear up to 15 hydroxyl groups and/or be interrupted by up to 14 non-adjacent oxygen atoms, $C_2$–$C_{30}$-alkenyl, $C_7$–$C_{18}$-aralkyl, $C_6$–$C_{14}$-aryl which can be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, or are each a group of the formula —$CR^1R^2$—$PO_3H_2$, —$CH_2$—COOH or —$CH_2$—CH(OH)—$R^1$, where at least one of the radicals $R^3$ to $R^6$ is the group —$CR^1R^2$—$PO_3H_2$ and at least a further one of these radicals is $C_6$–$C_{30}$-alkyl, $C_6$–$C_{30}$-alkenyl, $C_7$–$C_{18}$-aralkyl, unsubstituted or substituted $C_6$–$C_{14}$-aryl or the group —$CH_2$—CH(OH)—$R^9$, where $R^9$ is $C_6$–$C_{30}$-alkyl, $C_6$–$C_{30}$-alkenyl, $C_7$–$C_{18}$-aralkyl or unsubstituted or substituted $C_6$–$C_{14}$-aryl, and where $R^1$ and $R^2$ are as defined above, A is a $C_1$–$C_{12}$-alkylene group which can additionally bear as substituents up to three $C_1$–$C_{30}$-alkyl groups, $C_2$–$C_{30}$-alkenyl groups, $C_7$–$C_{18}$-aralkyl groups or $C_6$–$C_{14}$-aryl groups which can in turn be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, where, if a plurality of groups A are present, these can be identical or different, and p is a number from 0 to 30,000.

The compounds II can be in the form of monomers (p=0), oligomers or polymers.

Suitable straight-chain or branched alkyl radicals as $R^1$ to $R^9$ and as substituents on aryl groups, which are mentioned as $C_1$–$C_{30}$-, $C_6$–$C_{30}$- or $C_1$–$C_{12}$-alkyl radicals, are, for example, methyl, ethyl, n-propyl, iso-propyl-, n-butyl, iso-butyl, sec-butyl, tert-butyl, n-amyl, iso-amyl, sec-amyl, tert-amyl, neopentyl, n-hexyl, n-heptyl, n-octyl, 2-ethylhexyl, n-nonyl, iso-nonyl, n-decyl, n-undecyl, n-dodecyl, n-tridecyl, iso-tridecyl, n-tetradecyl, n-pentadecyl, n-hexadecyl, n-heptadecyl, n-octadecyl and n-eicosyl.

Suitable alkyl radicals additionally bearing up to 15, in particular up to 10, especially up to 5, hydroxyl groups and/or interrupted by up to 14, in particular by up to 9, especially by up to 4, non-adjacent oxygen atoms are, for example, corresponding polyoxyalkylene chains, in particular polyoxyethylene chains, whose terminal hydroxyl groups can be etherified by alkyl radicals, for example groups of the formula —$CH_2CH_2$—OH, —$CH_2CH_2$—O—$CH_3$, —$CH_2CH_2$—O—$CH_2CH_2$—OH, —$CH_2CH_2O$—$CH_2CH_2O$—$CH_3$, —$CH_2CH_2CH_2$—OH, —$CH_2CH_2CH_2$—O—$CH_2CH_3$, —$CH_2CH_2$—O—$CH_2CH_2$—O—$CH_2CH_2$—OH or —$CH_2CH_2$—O—$CH_2CH_2$—O—$CH_2CH_2$—OH.

Among these, preferred radicals as $R^1$ and $R^2$ and as substituents on aryl groups are in general lower alkyl radicals, in particular $C_1$–$C_{12}$-alkyl radicals, but especially $C_1$–$C_4$-alkyl radicals, in particular ethyl and methyl.

Particularly suitable long-chain $C_6$–$C_{30}$-alkyl radicals $R^3$ to $R^9$ are $C_8$–$C_{20}$-alkyl radicals. Here, radicals having a low degree of branching, ie. having up to 5 methyl or ethyl side chains, are often particularly effective.

Suitable straight-chain or branched $C_2$–$C_{30}$- or $C_6$–$C_{30}$-alkenyl radicals as $R^1$ to $R^9$ are, for example, vinyl, allyl, methallyl and but-2-enyl and also, as long-chain radicals, oleyl, linoleyl and linolenyl.

Suitable $C_7$–$C_{18}$-aralkyl radicals as $R^1$ to $R^{10}$ are, for example, naphthylmethyl, diphenylmethyl or methylbenzyl, but particularly $C_7$–$C_{18}$-phenylalkyl such as 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 10-phenyldecyl, 12-phenyldodecyl or especially benzyl.

Suitable $C_6$–$C_{14}$-aryl radicals as $R^1$ to $R^{10}$ are, for example, biphenyl, naphthyl, anthryl and especially phenyl, which can each be substituted as indicated. If such substituents are present on phenyl rings, the preferred degree of substitution is 2 or in particular 1. Monosubstituted phenyl radicals are substituted in the ortho, meta or preferably para positions, disubstituted phenyl radicals frequently have a 2,4 substitution pattern and trisubstituted phenyl radicals often have a 2,4,6 substitution pattern. If two or three substituents are present, these can be identical or different.

Typical substituents on the aryl radicals, in particular on the phenyl rings, are methyl groups (o-, m-, p-tolyl, 2,4-dimethylphenyl, mesityl), methoxy groups, methoxycarbonyl and ethoxycarbonyl groups.

Besides methoxy, further suitable straight-chain or branched $C_1$–$C_{12}$-alkoxy groups, in particular as substituents on the phenyl ring, are especially $C_2$–$C_4$-alkoxy groups such as ethoxy, n-propoxy, iso-propoxy, n-butoxy, iso-butoxy, sec-butoxy and tert-butoxy, but also n-pentoxy, n-hexoxy, iso-hexoxy, n-heptoxy, iso-heptoxy, n-octoxy, 2-ethylhexoxy, iso-octoxy, n-nonoxy, n-decoxy, n-undecoxy and n-dodecoxy.

For the purposes of the present invention, halogen atoms are fluorine, iodine, but especially bromine and in particular chlorine.

Groups of the formula —$CH_2$—CH(OH)—$R^9$ are derived, for example, from long-chain epoxidized α-olefins such as 1,2-epoxyhexane, 1,2-epoxyoctane, 1,2-epoxydecane, 1,2-epoxydodecane, 1,2-epoxytetradecane, 1,2-epoxyhexadecane or 1,2-epoxyoctadecane or from styrene oxide.

The bridge A is preferably a $C_2$–$C_8$-alkylene group, in particular a $C_3$–$C_6$-alkylene group. A can be branched or preferably straight-chain, ie. have a polymethylene structure. Typical examples of A are methylene, 1,2-ethylene, 1,2-propylene, 1,3-propylene, dimethylmethylene, ethylmethylene, 1,2-butylene, 1,3-butylene, 2,3-butylene, 1,4-butylene, pentamethylene, hexamethylene and octamethylene.

If a plurality of groups A are present, these can also be different, eg. the group of the formula

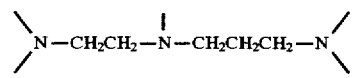

can be present as structural element.

If A is substituted by the radicals indicated, these substituents are as defined above for $R^1$ to $R^6$.

The degree of oligomerization or polymerization p is, in the case of oligomers, preferably from 0 to 20, in particular from 0 to 5, especially 0 or 1, and in the case of polymers is preferably from 20 to 30,000, in particular from 20 to 5000, especially from 20 to 100.

Typical examples of monomeric compounds II (p=0) are structures of the following types:

$(R^7)_2N$—$CH_2$—$PO_3H_2$ $H_2O_3P$—$CH_2$—$NR^7$—$CH_2$—$PO_3H_2$.

Typical examples of oligomeric compounds II (usually p=1) are structures of the following types:

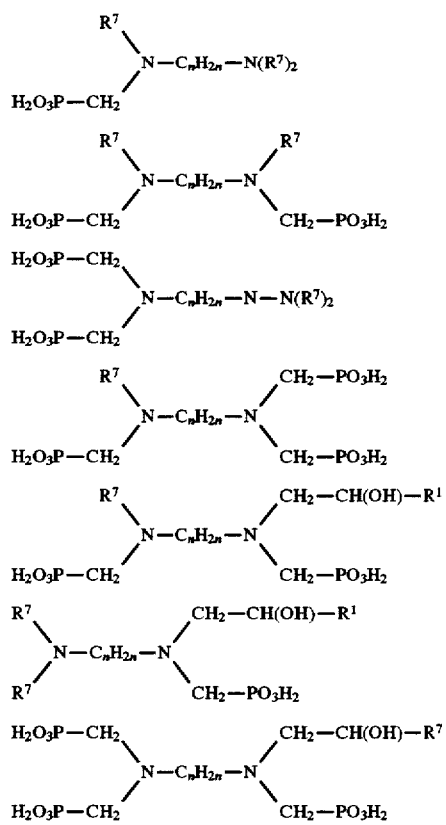

-continued

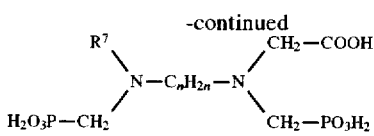

In these formulae, $R^7$ is $C_6$–$C_{30}$-alkyl or $C_6$–$C_{30}$-alkenyl, n is a number from 2 to 6 and $R^1$ is as defined above.

Typical examples of polymeric hydrocarbon-soluble aminomethylenephosphonic acid derivatives for the purposes of the present invention are polyalkylenepolyamines and polyalkylenepolyamides containing at least one group of the formula —$CR^1R^2$—$PO_3H_2$ and at least one further $C_6$–$C_{30}$-alkyl radical, $C_6$–$C_{30}$-alkenyl radical, $C_7$–$C_{18}$-aralkyl radical, unsubstituted or substituted $C_6$–$C_{14}$-aryl radical or a group of the formula —$CH_2$—$CH(OH)$—$R^9$, where $R^1$, $R^2$ and $R^9$ are as defined above, in particular correspondingly substituted polyethyleneimines, polyvinylamines and polyacrylamides, for example of the structure:

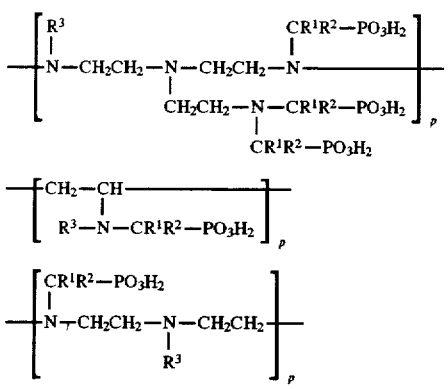

In these formulae, $R^3$ and p are as defined above.

The polyalkylenepolyamines described can have linear or branched structures. The bridges between the nitrogen atoms in the main polymer chain are preferably ethylene or propylene groups, but also methylene, butylene, pentylene or hexylene groups, or mixtures thereof.

To slightly modify the properties of the polyalkylenepolyamines described for the purposes of optimizing them for the application according to the present invention, these polymers can, to an appropriate degree, be functionalized with suitable end groups, crosslinked or made available as copolymers or graft polymers To introduce suitable end groups, the polyalkylenepolyamines can be reacted with $C_1$–$C_{30}$-alkyl halides, eg. methyl iodide, ethyl chloride or ethyl bromide, with benzyl halides, wit halohydrins, eg. chlorohydrin, with polyalkylene oxides, with epoxidized $\alpha$-$C_3$–$C_{30}$-olefins, with isocyanates or with $C_1$–$C_{30}$-monocarboxylic acids.

Suitable crosslinkers are, for example, epihalohydrins, eg. epichlorohydrin, $\alpha$,$\omega$-bis(epoxides), $\alpha$,$\omega$- or vicinal dichloroalkanes, eg. 1,2-dichloroethane, $C_2$–$C_{30}$-dicarboxylic acids, eg. adipic acid, and diisocyanates, eg. hexamethylene diisocyanate.

Suitable polyvinylamine copolymers comprise, for example, as other monoethylenically unsaturated monomers, vinyl esters of saturated carboxylic acids having from 1 to 6 carbon atoms, eg. vinyl acetate, vinyl propionate and vinyl butyrate, monoethylenically unsaturated $C_3$–$C_8$-carboxylic acids such as acrylic acid, methacrylic acid, dimethylacrylic acid, ethacrylic acid, crotonic acid, vinylacetic acid, allylacetic acid, maleic acid, fumaric acid, citraconic acid and itaconic acid and also their esters, anhydrides, amides and nitrites. Anhydrides which are preferably used are, for example, maleic anhydride, citraconic anhydride and itaconic anhydride. Suitable esters are derived, for example, from alcohols having from 1 to 6 carbon atoms, for example methyl acrylate, methyl methacrylate, ethyl acrylate, ethyl methacrylate, isobutyl acrylate and hexyl acrylate, or from glycols or polyalkylene glycols, where in each case only one OH group of the glycol or polyglycol is esterified with a monoethylenically unsaturated carboxylic acid, eg. hydroxyethyl acrylate, hydroxyethyl methacrylate, hydroxypropyl acrylate, hydroxypropyl methacrylate, hydroxybutyl acrylate, hydroxybutyl methacrylate and also acrylic monoesters of polyalkylene glycols having a molecular weight of up to 10,000. Also suitable are esters of the above carboxylic acids with aminoalcohols, eg. dimethylaminoethyl acrylate, dimethylaminoethyl methacrylate, diethylaminoethyl acrylate, diethylaminoethyl methacrylate, dimethylaminopropyl acrylate and dimethylaminopropyl methacrylate. Suitable amides are, for example, acrylamides and methacrylamides such as N-alkylamides and N,N-dialkylamides having alkyl radicals of from 1 to 6 carbon atoms, eg. N-methylacrylamide, N,N-dimethylacrylamide, N-methylmethacrylamide, N-ethylacrylamide, N-propylacrylamide and tert-butylacrylamide and also basic amides such as dimethylaminoethylacrylamide, dimethylaminoethylmethacrylamide, diethylaminoethylmethacrylamide, diethylaminoethylacrylamide, dimethylaminopropylacrylamide, diethylaminopropylacrylamide, diethylaminopropylmethacrylamide and dimethylaminopropylmethacrylamide. The basic acrylates and acrylamides can be used in the form of the free bases, the salts with mineral acids or carboxylic acids or else in quaternized form. Also suitable as comonomers are acrylonitrile, methacrylonitrile, N-vinylpyrrolidone, N-vinylcaprolactam, N-vinylimidazole and also substituted N-imidazoles such as N-vinyl-2-methylimidazole and N-vinyl-2-ethylimidazole and N-vinylimidazoline and substituted N-vinylimidazolines, eg. N-vinyl-2-methylimidazoline. Apart from the monomers mentioned, it is also possible to use monomers containing sulfo groups, for example vinylsulfonic acid, allylsulfonic acid, styrenesulfonic acid and 3-sulfopropyl esters of acrylic acid as other monoethylenically unsaturated monomers.

The copolymers specified have K values of from 10 to 300, preferably from 20 to 200. The K values are determined by the method of H. Fikentscher in 5% strength aqueous sodium chloride solution at pH 7, 25° C. and a polymer concentration of 0.1% by weight.

It is also possible to use polyethyleneimines grafted onto polyvinylamines.

For the use according to the present invention of the compounds II and the specified polyalkylenepolyamines the presence of at least one methylenephosphonic acid group —$CR^1R^2$—$PO_3H_2$ and at least one hydrophobic radical, ie. an aromatic group or preferably a saturated or unsaturated long-chain aliphatic radical ($C_6$–$C_{30}$-alk(en)yl), is of decisive importance. The methylenephosphonic acid groups are essentially responsible for the selective complexation (extraction) of the iron ions and the hydrophobic radicals make the compounds soluble in hydrocarbons.

The hydrocarbon-soluble aminomethylenephosphonic acid derivatives to be used according to the present invention can be prepared by customary methods. Compounds having $R^1$=$R^2$=hydrogen can be obtained most simply by reacting appropriate amines with formaldehyde (or paraformaldehyde) and phosphorous acid with acid catalysis (eg. inorganic acids or mineral acids such as sulfuric acid or hydrochloric acid, sulfonic acids such as p-toluenesulfonic acid or methanesulfonic acid or carboxylic acids such as a mixture of acetic acid and acetic anhydride).

Such reactions of amines with formaldehyde and phosphorous acid are usually carried out at from 0 to 150° C., in particular from 50 to 120° C., especially from 80 to 110° C. Amine, formaldehyde and phosphorous acid are advantageously used in a molar ratio of 1:(2–6):(1–4) based on one N—H bond.

Alternatively, these compounds can also be obtained by hydrolysis of the corresponding phosphonic esters, obtainable by reaction with phosphites in place of phosphorous acid.

Another synthetic route which is of particular interest for compounds having $R^1$, $R^2 \neq H$ starts out from aldehydes (eg. of the formula $R^1$—CHO) or ketones (eg. of the formula $R^1$—CO—$R^2$) and the appropriate primary amines which are reacted to form imines onto which phosphorous acid is then added.

The term solvent extraction customarily refers to extraction processes in which two liquid phases which are sparingly miscible or immiscible with one another are brought into intimate contact and a transfer of one or more components, here iron ions, from one phase into the other takes place. In this process, an equilibrium dependent on various external parameters is usually established. Important parameters in this context are the residence time (contact time), the temperature, the concentration (composition of the mixture) and the pH.

In the aqueous solutions of desired metals to be worked up, the interfering iron is generally present as iron(III) ions. The solvent extraction according to the present invention gives particularly good results if the aqueous solutions concerned are strongly acid, ie. have a pH of from less than 0 to 6, in particular from –1 to 3, especially from –0.5 to 1.5. Usual iron(III) contents in such aqueous, acid solutions of desired metals are from 0.005 to 100 g/l, in particular from 0.5 to 40 g/l, calculated as iron(III) sulfate; in addition, from 50 to 250 g/l of acids (usually mineral acids), eg. from about 70 to 100 g/l of sulfuric acid (calculated on a 100% basis) are generally added.

The contact time is usually from 1 to 60 minutes, in particular from 10 to 30 minutes. The temperature during the extraction is normally in the range from 20° to 80° C., in particular from 40° to 60° C.

For the purposes of the present invention, organic solutions of the aminomethylenephosphonic acid derivatives described are used. Suitable organic solvents are, for example, aliphatic, cycloaliphatic or aromatic hydrocarbons or mixtures of these having a high boiling point, halogenated hydrocarbons, ketones or ethers having a high boiling point or else mixtures of such compounds. Preference is given to using petroleum hydrocarbons such as kerosene.

The monomeric and oligomeric aminomethylenephosphonic acid derivatives described generally have a concentration in the specified organic solvents of from 0.01 to 8 mol/l, in particular from 0.05 to 3 mol/l, especially from 0.1 to 1 mol/l. Polymeric aminomethylenephosphonic acid derivatives such as the corresponding polyethyleneimine or polyvinylamine derivatives generally have concentrations of from 0.5 to 800 g/l, in particular from 5 to 600 g/l, especially from 50 to 300 g/l.

Finally, the mass ratios of organic and aqueous phases used also play a role, with the ratios of organic phase to aqueous phase generally being from 1:10 to 10:1, preferably from 1:3 to 3:1, in particular from 1:2 to 2:1.

The solvent extraction of the present invention can be carried out on a laboratory scale or on an industrial scale, batchwise or continuously (eg. in a mixer settler plant or in pulsed columns).

The separation of the iron extracted from the organic solutions and the recovery of the extractants (complexing agents) used and any further auxiliaries concomitantly used can be carried out by conventional methods.

In addition to the actual extractants (complexing agents), "modifiers" are usually used in the solvent extraction. The term "modifiers" refers to compounds which either effect a better or more rapid phase separation, accelerate the transfer of the components to be extracted from one phase-to the other or improve the solubility of the metal complex formed in the organic diluent phase. Modifiers known from the prior art are, for example, straight-chain or branched long-chain alcohols having from 10 to 22 carbon atoms, for example isodecanol, isotridecanol or hexadecanol, phenols or esters of such alcohols and phenols with lower carboxylic acids or relatively long-chain fatty acids.

Specifically for the aminomethylenephosphonic acid derivatives described for the solvent extraction of iron ions, we have developed new modifiers which can be used with excellent results together with these and other extractants for separating off iron and also other metals such as cobalt, copper, vanadium, cadmium, nickel, zinc, lead, aluminum, uranium, antimony, chromium, manganese, silver, palladium, rhodium, platinum, mercury, plutonium or bismuth.

These novel modifiers are an alkoxylated long-chain alcohol of the general formula III

or an alkoxylated long-chain amine of the general formula IV

where $R^7$ is $C_6$–$C_{30}$-alkyl, in particular $C_8$–$C_{20}$-alkyl, or $C_6$–$C_{30}$-alkenyl, in particular $C_8$–$C_{20}$-alkenyl, $C_7$–$C_{18}$-aralkyl or $C_6$–$C_{14}$-aryl which may be unsubstituted or substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups.

$R^8$ is hydrogen, $C_1$–$C_5$-alkyl, $C_2$–$C_5$-alkenyl or the group —(XO)$_m$—H or is as defined for $R^7$, X is a 1,2-alkylene group having from 2 to 30 carbon atoms, in particular from 2 to 4 carbon atoms, or a group of the formula —CH$_2$—CHR$^{10}$13 , where $R^{10}$ is $C_7$–$C_{18}$-aralkyl or $C_6$–$C_{14}$-aryl which may be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, and m is a number from 1 to 20, in particular from 2 to 10.

The modifiers III and IV can be prepared by known methods by alkoxylation of the corresponding alcohols or amines, for example using ethylene oxide, propylene oxide, butylene oxide or styrene oxide.

Since alkoxylations generally produce mixtures of alkoxides, the degree of alkoxylation m is usually a mean value. These mixtures may also still contain unreacted alcohol $R^7$—OH or unreacted amine $R^7R^8N$—H (in which case m=0).

Both the known modifiers and also the novel modifiers are used together with the extractant (complexing agent) in a weight ratio of extractant to modifier of from 99.5:0.5 to 0.5:99.5, preferably from 95:5 to 5:95, in particular from 80:20 to 20:80. It is also possible to use mixtures of various types of modifiers. They are employed in the abovementioned organic solvents.

The present invention also provides mixtures suitable for the solvent extraction of iron ions from aqueous solution and comprising A) from 0.5 to 99.5% by weight of one or more of the hydrocarbon-soluble aminomethylenephosphonic acid derivatives described and B) from 99.5 to 0.5% by weight of one or more alkoxylated long-chain alcohols III and/or amines IV.

These mixtures are, as described, employed in the abovementioned organic solvents.

Since the modifiers of the structure III and IV are in principle new substances for this application, the present invention also provides for the use of alkoxylated long-chain alcohols of the general formula III

$$R^7-(XO)_m-H \quad (III)$$

or alkoxylated long-chain amines of the general formula IV

$$\begin{array}{c} R^7 \\ \phantom{R^7}\diagdown \\ \phantom{R^7}N-(XO)_m-H \\ \phantom{R^7}\diagup \\ R^8 \end{array} \quad (IV)$$

where $R^7$ is $C_6$–$C_{30}$-alkyl, $C_6$–$C_{30}$-alkenyl, $C_7$–$C_{18}$-aralkyl or $C_6$–$C_{14}$-aryl which may be unsubstituted or substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, $R^8$ is hydrogen, $C_1$–$C_5$-alkyl, $C_2$–$C_5$-alkenyl or the group —(XO)$_m$—H or is as defined for $R^7$.

X is a 1,2-alkylene group having from 2 to 30 carbon atoms, in particular from 2 to 4 carbon atoms, or a group of the formula —CH$_2$–CHR$^{10}$—, where $R^{10}$ is $C_7$–$C_{18}$-aralkyl or $C_6$–$C_{14}$-aryl which may be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, and m is a number from 1 to 20, as modifiers in the solvent extraction of metal ions, in particular iron ions, from aqueous solutions.

The hydrocarbon-soluble aminomethylenephosphonic acid derivatives used according to the present invention as extractants in solvent extraction make it possible to selectively remove iron ions to a high degree of efficiency from aqueous solutions of desired metals comprising, for example, zinc or copper as desired metal. The loading capacity of the extractant of the present invention is above average. The concomitant use of the novel modifiers of the structures III and IV further improves the already excellent results.

EXAMPLES

Preparation of the Aminomethylenephosphonic Acid Derivatives

Unless otherwise indicated, percentages given below are by weight.

The reaction products described below were separated off directly as organic phase, extracted with an organic solvent in which they are soluble or salted out of the aqueous phase using sodium sulfate and subsequently repeatedly washed with water. The degree of phosphonomethylation was determined from the P/N ratio by means of elemental analysis.

Example 1

Reaction Product of di-2-ethylhexylamine with Phosphorous Acid and Formaldehyde 289.8 g (1.20 mol) of di-2-ethylhexylamine were initially charged and 118.1 g (1.44 mol) of phosphorous acid dissolved in 160 ml of water were added dropwise. Subsequently, 85.2 g of concentrated sulfuric acid which had been diluted with 75 ml of water were added. The mixture obtained was heated to about 100° C. and 247 g (3.0 mol) of aqueous formaldehyde solution (36.5% strength) were added dropwise. The mixture was refluxed for 40 hours and the organic phase was then separated off and washed 3 times with 500 ml each time of water. Remaining water in the washed organic phase was removed in a water pump vacuum. Yield: 370 g of a yellow viscous oil (92% of theory); by-product: methyldi(2-ethylhexylamine); elemental analysis: $P_{found}$ 7.1%, $N_{found}$ 4.3%.

Example 2

Reaction Product of Diisotridecylamine with Phosphorous Acid and Formaldehyde 450 g (1.18 mol) of diisotridecylamine were initially charged and 98.4 g (1.20 mol) of phosphorous acid dissolved in 240 ml of water were added dropwise. Subsequently, 276.7 g of concentrated sulfuric acid which had been diluted with 90 ml of water were added. The mixture obtained was heated to about 100° C. and 197 g (2.4 mol) of aqueous formaldehyde solution (36.5% strength) were added dropwise. The mixture was refluxed for 40 hours. The organic phase was separated off and washed 6 times with 750 ml of water. The remaining water in the washed organic phase was removed in a water pump vacuum. Yield: 484 g of yellow viscous oil (85% of theory); by-product: methyldiisotridecylamine; elemental analysis: $P_{found}$ 5.2%, $N_{found}$ 3.0%.

Example 3

Reaction Product of N-oleylpropylenediamine with Phosphorous Acid and Formaldehyde 99.2 g (0.31 mol) of N-oleylpropylenediamine were initially charged and 147.6 g (1.8 mol) of phosphorous acid dissolved in 360 ml of water were added dropwise. Subsequently, 300 g of concentrated sulfuric acid which had been diluted with 95 ml of water were added. The mixture obtained was heated to about 100° C. and 296 g (3.6 mol) of aqueous formaldehyde solution (36.5% strength) were added dropwise. The mixture was stirred further for 25 hours at about 100° C. The product was completely salted out using sodium sulfate, separated off and washed 3 times with 750 ml of water. Remaining water was removed in a water pump vacuum. Yield: 175 g of a yellowish brown solid (96% of theory); methylation by-products; elemental analysis: $P_{found}$ 11.6, $N_{found}$ 3.6%.

Example 4

Reaction Product of N-oleylpropylenediamine with 1-epoxydodecane and Subsequently with Phosphorous Acid and Formaldehyde 99.2 g (0.31 mol) of N-oleylpropylenediamine and 100 g of toluene were initially charged and heated to 100° C. Subsequently, 55.2 g (0.30 mol) of 1-epoxydodecane were added dropwise and the mixture was stirred further under reflux until epoxide could no longer be detected (Preußmann test). The product obtained was freed of solvent and reacted further.

53.8 g of the product obtained (0.106 mol) were initially charged and heated to 50° C. Subsequently, 32.8 [lacuna] (0.4 mol) of phosphorous acid diluted with 80 ml of water and 92 g of concentrated sulfuric acid which had previously been diluted with 80 g of water were added The temperature was increased to 100° C. and 66 g (0.79 mol) of aqueous formaldehyde solution (36.5%) and an additional 300 ml of water were added. Subsequently, the reaction mixture was stirred further for about 96 hours at 95° C. The organic solid was separated off and washed a number of times with water. Remaining water was removed in a water pump vacuum. Yield: 58 g of brown solid (80% of theory); analysis: $P_{found}$ 4.9%, $N_{found}$ 3.6%.

Extraction Tests

Extractability of iron(III) ions from aqueous solutions strongly acid with sulfuric acid was confirmed by tests carried out batchwise (batch stirring experiments). The ratios by mass between organic and aqueous phase were about 1:2 or 2:1. The extractions were carried out at about 50° C. The organic complexing agent was dissolved in kerosine, admixed with modifiers and brought into intimate contact with an aqueous solution comprising the iron ions and free sulfuric acid, the iron going from the aqueous phase into the organic phase. The phases were separated and the metal contents were determined by means of atomic absorption spectroscopy (flame AAS).

Example 5
Determination of Loading Capacities for Fe(III) in the Organic Extraction Phase The tests were carried out as batch stirring experiments in a stirred flask. 100 g of a synthetic aqueous Fe(III) solution (composition: 30 g/kg of Fe(III), dissolved as iron(III) sulfate, and 85 g/l of free sulfuric acid) were mixed for 10 minutes at 50° C. with 50 g of organic phase (composition: 7.5% of extractant, 5–20% of modifiers and 87.5–72.5% of kerosine*)). Subsequently, the phases were separated and the metal contents of the organic phase were determined by means of flame AAS. Mono-2-ethylhexyl 2-ethylhexylphosphonate as described in (1) were employed for comparison. The product from Example 3 in combination with the modifier B1 developed specifically for this complexing agent gave the highest loading capacity for Fe(III) in the organic phase.

Table 1 shows the results of these determinations:

| Extractant (complexing agent) [7.5%] | Modifier [%] | Fe content of the organic phase [%] |
|---|---|---|
| Product from Example 1 | B2 [10] | 0.60–0.70 |
| Product from Example 2 | B2 [5] | 0.50–0.55 |
| Product from Example 3 | B1 [20] | 1.30–1.40 |
| Product from Example 4 | B1 [5] + B2 [5] | 0.50–0.60 |
| For comparison: | | |
| Mono-2-ethylhexyl 2-ethylhexylphosphonate | B1 [20] | 0.03 |
| Mono-2-ethylhexyl | B2 [5] | 0.10 |

| Extractant (complexing agent) [7.5%] | Modifier [%] | Fe content of the organic phase [%] |
|---|---|---|
| 2-ethylhexyl phosphonate | | |

B1 = diisotridecylamine reacted with 2.1 mol of ethylene oxide
B2 = isodecanol
*) Kerosine in accordance with DIN 51 636 (from Wintershall):
Boiling range   180–250° C.
Density (15° C.)   0.798 g/cm³
Viscosity (20° C.)   2 mm²/s (cSt)
Flashpoint AP   >55° C.
Aromatics content (FIA)   13%

Example 6

Concentration-dependent Determination of Fe(III) Loading Capacity in the Organic Phase, Zn(II) Coextraction Studies To study the influence of the complexing agent concentration on the Fe(III) loading capacity in the organic phase, in each case 50 g of organic phase (composition: 7.5–25% of the respective complexing agent, 10–33% of modifier, 42–82.5% of kerosine*)) and 100 g of aqueous phase (composition: 2.7% of Fe(III) dissolved as iron(III) sulfate, 6.3% of Zn(II) dissolved as zinc(II) sulfate and 85 g/l of sulfuric acid (conc.)) were intimately mixed for 10 minutes at 50° C. in a stirred flask, the phases were separated and the metal contents were determined by means of atomic absorption spectroscopy (flame AAS). Fe(III) loading capacities of about 2% were achieved. The compounds studied showed good Fe(III) selectivity from Fe(III)/Zn(II) mixed solutions.

Table 2 shows the results of this determination:

| Extractant (complexing agent) [%] | Modifier [%] | Content of Fe and Zn in the organic phase [%] |
|---|---|---|
| Product from Example 1 | [7.5] | B2 [10] | 0.61% Fe (<0.1% Zn) |
| | [15] | B2 [20] | 1.10% Fe (<0.1% Zn) |
| | [25] | B2 [33] | 1.95% Fe (<0.1% Zn) |
| Product from Example 3 | [7.5] | B1 [20] | 1.36% Fe (<0.15% Zn) |
| | [10] | B1 [20] | 1.82% Fe (<0.20% Zn) |
| | [15] | B1 [20] | 2.32% Fe (<0.25% Zn) |

Example 7

Fe(III) Separation at an Organic to Aqueous Mass Ratio of 1:2

To study the influence of the phase ratios on the Fe(III) extraction, in each case 50 g of organic phase (composition: 7.5% of complexing agent, 5–20% of modifier, 72.5–87.5% of kerosine*)) and 100 g of aqueous phase (composition: 0.4% of Fe(III) dissolved as iron(III) sulfate and 85 g/l of sulfuric acid) were intimately mixed for 10 minutes at 50° C. in a stirred flask, the phases were separated and the residual Fe contents in the aqueous phase were determined by means of flame AAS. The product from Example 3 was able to remove virtually all Fe(III) from the aqueous solution which was strongly acid with sulfuric acid.

Table 3 shows the results of these determinations:

| Extractant (complexing agent) [7.5%] | Modifier [%] | Content of Fe in the aqueous phase [%] |
|---|---|---|
| Product from Example 1 | B2 [10] | 0.15 |
| Product from Example 2 | B2 [5] | 0.20 |
| Product from Example 3 | B1 [20] | <0.01 |
| Product from Example 4 | B1 [5] + B2 [5] | 0.17 |

Example 8
Fe(III) Removal at an Organic to Aqueous Mass Ratio of 2:1

To study the influence of the phase ratios on the Fe(III) extraction, in each case 100 g of organic phase (composition: 7.5% of complexing agent, 5–20% of modifier, 72.5–87.5% of kerosine*)) and 50 g of aqueous phase (composition: 1.46% of Fe(III) dissolved as iron(III) sulfate and 85 g/l of sulfuric acid) were intimately mixed for 10 minutes at 50° C. in a stirred flask, the phases were separated and the residual Fe contents in the aqueous phase were determined by means of flame AAS. Here too, the product from Example 3 was able to remove virtually all Fe(III) from the aqueous solution which was strongly acid with sulfuric acid.

Table 4 shows the results of these determinations:

| Extractant (complexing agent) [7.5%] | Modifier [%] | Content of Fe in the aqueous phase [%] |
|---|---|---|
| Product from Example 1 | B2 [10] | 0.39 |
| Product from Example 2 | B2 [5] | 0.50 |
| Product from Example 3 | B1 [20] | <0.01 |
| Product from Example 4 | B1 [5] + B2 [5] | 0.40 |

We claim:

1. A process for the solvent extraction of iron ions from aqueous solutions, which comprises extracting an aqueous solution containing iron ions with a solvent containing a hydrocarbon-soluble aminomethylenephosphonic acid having a structural element of formula (I)

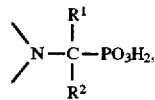

where $R^1$ and $R^2$ are hydrogen, $C_1$–$C_{30}$-alkyl which can additionally bear up to 15 hydroxyl groups and/or be interrupted by up to 14 non-adjacent oxygen atoms, $C_2$–$C_{30}$-alkenyl, $C_7$–$C_{18}$-aralkyl or $C_6$–$C_{14}$-aryl which can be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups.

2. The process of claim 1, wherein said hydrocarbon-soluble aminomethylenephosphonic acid comprises a structural element of formula (Ia)

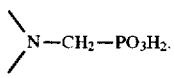

3. The process of claim 1, wherein said hydrocarbon-soluble aminomethylenephosphonic acid has formula (II)

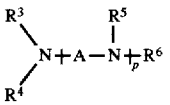

where $R^3$ to $R^6$ are each hydrogen, $C_1$–$C_{30}$-alkyl which can additionally bear up to 15 hydroxyl groups and/or be interrupted by up to 14 non-adjacent oxygen atoms, $C_2$–$C_{30}$-alkenyl, $C_7$–$C_{18}$-aralkyl, $C_6$–$C_{14}$-aryl which can be substituted by up to three $C_1$–$C_{12}$-alkyl groups, $C_1$–$C_{12}$-alkoxy groups, halogen atoms, cyano groups, hydroxy groups or $C_1$–$C_4$-alkoxycarbonyl groups, or are each a group of the formula —$CR^1R^2$—$PO_3H_2$, —$CH_2$—COOH or —$CH_2$—CH(OH)—$R^1$, where at least one of the radicals $R^3$ to $R^6$ is the group —$CR^1R^2$—$PO_3H_2$ and at least a further one of said radicals is $C_6$–$C_{30}$-alkyl, $C_6$–$C_{30}$-alkenyl, $C_7$–$C_{18}$-aralkyl, unsubstituted or substituted $C_6$–$C_{14}$-aryl or the group —$CH_2$—CH(OH)—$R^9$, where $R^9$ is $C_6$–$C_{30}$-alkyl, $C_6$–$C_{30}$-alkenyl, $C_7$–$C_{18}$-aralkyl or unsubstituted or substituted $C_6$–$C_{14}$-aryl, and where $R^1$ and $R^2$ are as defined above, A is a $C_1$–$C_{12}$-alkylene group which can additionally bear as substituents up to three $C_1$–$C_{30}$-alkyl groups, $C_2$–$C_{30}$-alkenyl groups, $C_7$–$C_{18}$-aralkyl groups or $C_6$–$C_{14}$-aryl groups which can in turn be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, where, if a plurality of groups A are present, these can be identical or different, and p is a number from 0 to 30,000.

4. The process of claim 1, wherein said hydrocarbon-soluble aminomethylenephosphonic acid comprises a polyalkylenepolyamine or polyalkylenepolyamide containing at least one group of the formula —$CR^1R^2$—$PO_3H_2$ and at least one further $C_6$–$C_{30}$-alkyl radical, $C_6$–$C_{30}$-alkenyl radical, $C_7$–$C_{18}$-aralkyl radical, unsubstituted or substituted $C_6$–$C_{14}$-aryl radical or a group of the formula —$CH_2$—CH(OH)—$R^9$, where $R^1$, $R^2$ and $R^9$ are as defined above.

5. The process of claim 1, comprising extracting from strongly acid aqueous solutions having a pH of from less than 0 to 6.

6. The process of claim 1, wherein the solvent further comprises an alkoxylated long-chain alcohol of the formula (III)

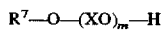

or an alkoxylated long-chain amine of the formula (IV)

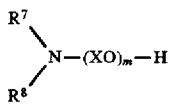

where $R^7$ is $C_6$–$C_{30}$-alkyl, $C_6$–$C_{30}$-alkenyl, $C_7$–$C_{18}$-aralkyl or $C_6$–$C_{14}$-aryl which may be unsubstituted or substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, $R^8$ is hydrogen, $C_1$–$C_5$-alkyl, $C_2$–$C_5$-alkenyl or a group —(XO)$_m$—H or is as defined for $R_7$, X is a 1,2-alkylene group having from 2 to 30 carbon atoms or a group of the formula —CH$_2$—CHR$^{10}$—, where $R^{10}$ is $C_7$–$C_{18}$-aralkyl or $C_6$–$C_{14}$-aryl which may be substituted by up to three $C_1$–$C_{12}$-alkoxy groups, halogen atoms, cyano groups, hydroxyl groups or $C_1$–$C_4$-alkoxycarbonyl groups, and m is a number from 1 to 20.

7. A mixture suitable for the solvent extraction of iron ions from aqueous solutions, comprising A) from 0.5 to 99.5% by weight of one or more hydrocarbon-soluble aminomethylenephosphonic acids as claimed in claim 1 and B) from 99.5 to 0.5% by weight of one or more of an alkoxylated long-chain alcohol III, $$R^7\text{—O—}(XO)_m\text{—H} \qquad (III)$$

or an alkoxylated long-chain amine of the formula (IV), or a mixture thereof where

 (IV)

where $R^7$ is $C_6$–$C_{30}$-alkyl, $C_6$–$C_{30}$-alkenyl, $C_7$–$C_{18}$-aralkyl or $C_6$–$C_{14}$-aryl which may be unsubstituted or substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, $R^8$ is hydrogen, $C_1$–$C_5$-alkyl, $C_2$–$C_5$-alkenyl or a group —(XO)$_m$—H or is as defined for $R^7$, X is a 1,2-alkylene group having from 2 to 30 carbon atoms or a group of the formula —CH$_2$—CHR$^{10}$—, where $R^{10}$ is $C_7$–$C_{18}$-aralkyl or $C_6$–$C_{14}$-aryl which may be substituted by up to three $C_1$–$C_{12}$-alkoxy groups, halogen atoms, cyano groups, hydroxyl groups or $C_1$–$C_4$-alkoxycarbonyl groups, and m is a number from 1 to 20.

8. A process for the solvent extraction of metal ions from aqueous solutions, which comprises extracting with a solvent containing an alkoxylated long-chain alcohol of formula (III)

$$R^7\text{—O—}(XO)_m\text{—H}$$

or an alkoxylated long-chain amine of formula (IV)

 (IV)

where $R^7$ is $C_6$–$C_{30}$-alkyl, $C_6$–$C_{30}$-alkenyl, $C_7$–$C_{18}$-aralkyl or $C_6$–$C_{14}$-aryl which may be unsubstituted or substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, $R^8$ is hydrogen, $C_1$–$C_5$-alkyl, $C_2$–$C_5$-alkenyl or a group —(XO)$_m$—H or is as defined for $R^7$, X is a 1,2-alkylene group having from 2 to 30 carbon atoms or a group of the formula —CH$_2$—CHR$^{10}$—, where $R^{10}$ is $C_7$–$C_{18}$-aralkyl or $C_6$–$C_{14}$-aryl which may be substituted by up to three $C_1$–$C_{12}$-alkyl groups, $C_1$–$C_{12}$-alkoxy groups, halogen atoms, cyano groups, hydroxyl groups or $C_1$–$C_4$-alkoxycarbonyl groups, and m is a number from 1 to 20.

* * * * *

UNITED STATES PATENT AND TRADEMARK OFFICE
CERTIFICATE OF CORRECTION

PATENT NO. : 5,795,482
DATED : August 18, 1998
INVENTOR(S) : Michael EHLE et al.

It is certified that error appears in the above-identified patent and that said Letters Patent is hereby corrected as shown below:

On the Title page, Item [86], PCT information should be:

-- PCT No.: PCT/EP95/02327

§ 371 Date: Jan. 8, 1997

§ 102(e) Date: Jan. 8, 1997 --

Signed and Sealed this

Second Day of March, 1999

Attest:

Q. TODD DICKINSON

*Attesting Officer*     Acting Commissioner of Patents and Trademarks